United States Patent
Blomqvist

(10) Patent No.: US 8,457,726 B2
(45) Date of Patent: Jun. 4, 2013

(54) HEART FAILURE DETECTING MEDICAL DEVICE

(75) Inventor: Andreas Blomqvist, Spånga (SE)

(73) Assignee: St. Jude Medical, AB, Jarfalla (SE)

( * ) Notice: Subject to any disclaimer, the term of this patent is extended or adjusted under 35 U.S.C. 154(b) by 331 days.

(21) Appl. No.: 12/933,612

(22) PCT Filed: Apr. 29, 2008

(86) PCT No.: PCT/SE2008/000298
§ 371 (c)(1), (2), (4) Date: Sep. 20, 2010

(87) PCT Pub. No.: WO2009/134170
PCT Pub. Date: Nov. 5, 2009

(65) Prior Publication Data
US 2011/0028855 A1 Feb. 3, 2011

(51) Int. Cl.
*A61B 5/04* (2006.01)
(52) U.S. Cl.
USPC ......................................... 600/513
(58) Field of Classification Search
USPC ......................... 600/508, 513, 515
See application file for complete search history.

(56) References Cited

U.S. PATENT DOCUMENTS

| | | | |
|---|---|---|---|
| 7,035,684 B2 | 4/2006 | Lee | |
| 7,190,996 B2 | 3/2007 | Järverud | |
| 7,778,697 B2 | 8/2010 | Björling et al. | |
| 2004/0078060 A1 | 4/2004 | Ding et al. | |
| 2005/0215914 A1* | 9/2005 | Bornzin et al. | 600/508 |
| 2006/0224203 A1 | 10/2006 | Hettrick et al. | |
| 2007/0055170 A1 | 3/2007 | Lippert et al. | |
| 2007/0093874 A1 | 4/2007 | Chirife et al. | |
| 2007/0179390 A1 | 8/2007 | Schecter | |
| 2009/0030292 A1 | 1/2009 | Bartnik et al. | |

FOREIGN PATENT DOCUMENTS

EP    1 078 597 A2    2/2001

* cited by examiner

*Primary Examiner* — Eric D. Bertram

(57) ABSTRACT

An implantable medical device has an event detector that detects a predetermined cardiac event during a heart cycle of a subject. A reference time is assigned to this detected cardiac event. An onset detector detects the onset of ventricular filling of the heart during the heart cycle. The relative time of the detected filling onset is determined based on the assigned time reference. An increased risk of heart failure of the subject is automatically determined based on the determined relative time for the filling onset. Generally, a reduction in the relative time, as determined at different points in time, indicates an increased heart failure risk or the presence of a heart failure condition.

10 Claims, 8 Drawing Sheets

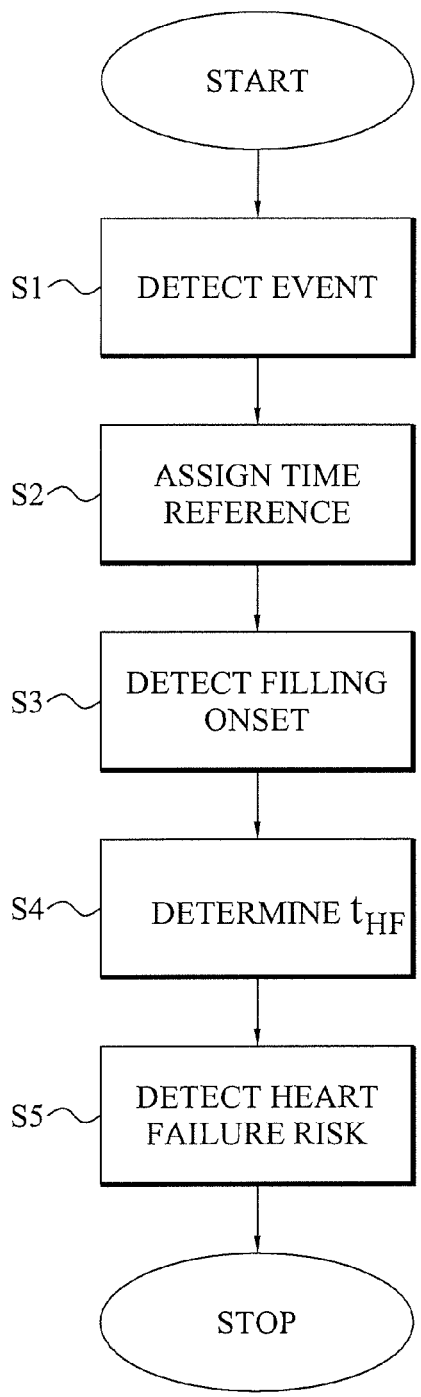
Fig. 9
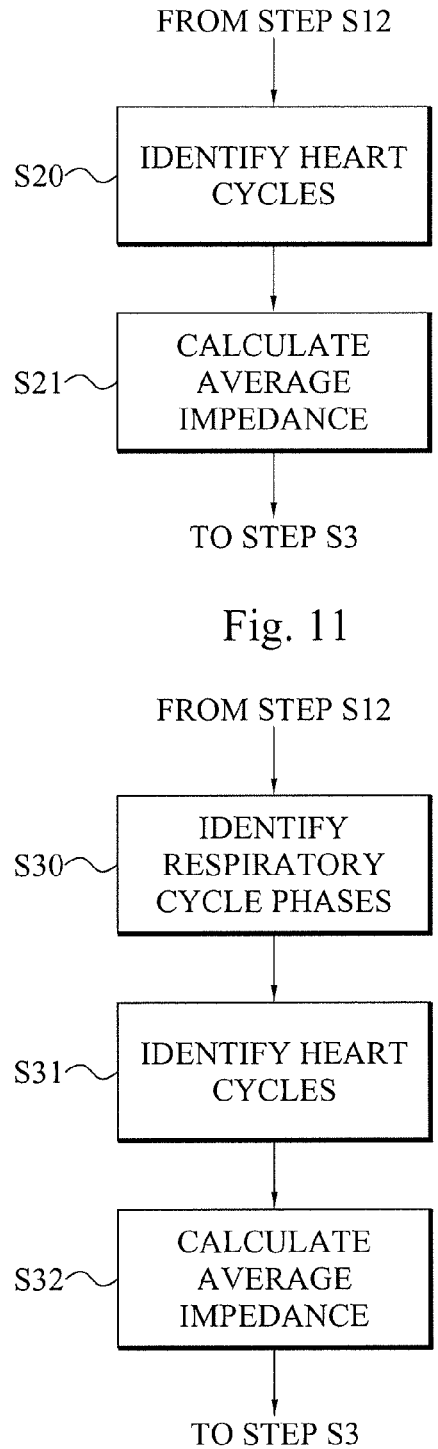
Fig. 11
Fig. 12

HEART FAILURE DETECTING MEDICAL DEVICE

BACKGROUND OF THE INVENTION

1. Field of the Invention

The present invention generally relates to implantable medical devices, and in particular such medical devices allowing an early detection of heart failure in subjects.

2. Description of the Prior Art

The heart is an essential organ in humans and most animals, pumping blood throughout the human/animal body. As a consequence, it is fundamentally important that the mechanical pumping properties of the heart operate correctly.

Heart failure is a condition that can result from a structural or functional cardiac disorder that impairs the ability of the heart to fill with or pump a sufficient amount of blood through the body.

Today, ejection fraction (EF) is the measure most commonly associated with heart failure (HF) diagnostics. There is a large population of the heart failure patients who have a preserved ejection-fraction (HFPEF-HF with preserved EF, HFNEF-HF with normal EF, or DHF—diastolic heart failure), but still some two thirds of the heart failure population have a decreased ejection fraction. When the ejection fraction starts to drop to detectable levels, such as below 40%, the patient is already severely ill. The reason for this is that the body in general and the heart in particular have many ways to counteract the failing systolic function. This makes the ejection fraction drop only detectable quite late in the disease progression. As a consequence, it is difficult to spot the degradation before the patient has progressed long in the heart failure condition.

There is therefore a need for an early detection of heart failure that can be used instead of or as a complement to the more late ejection fraction based HF-detection.

SUMMARY OF THE INVENTION

The present invention overcomes these and other drawbacks of the prior art arrangements.

It is a general object of the present invention to provide an implantable medical device having heart failure detecting functionality.

It is another object of the invention to provide an early heart failure assessment or diagnosis.

Briefly, the present invention involves an implantable medical device (IMD) capable of detecting a heart failure condition at an early state in the disease progression.

The IMD of the invention includes an event detector arranged for detecting occurrence of a predefined cardiac event during a heart cycle of the subject's heart. The predefined event occurs in a detection time window from the start of the heart cycle up to opening of the aortic valves in heart cycle. This event is preferably detected based on electric signals sensed from at least a portion of the heart. A preferred such cardiac event is the QRS complex or event of a heart cycle.

A time reference is assigned to the detected cardiac event. The IMD therefore preferably has a timer assigner that associates the time reference to a measured sample coinciding in time with the detected event. In such a case, the event-associated sample could be regarded as a starting time reference.

The IMD also includes an onset detector arranged for detecting the onset of ventricular filling of the heart in the heart cycle. The onset detector can be implemented for processing an impedance signal representative of the impedance measured over at least a portion of the heart. A timing processor determines a relative time of the detected filling onset. This time determination is preferably implemented by identifying a data sample coinciding in time with the onset of ventricular filling. The relative time is then determined based on the respective sample numbers of the filling onset and the predefined cardiac event and the previously assigned time reference.

The relative time is employed by a heart failure processor as a diagnostic parameter indicative of the presence of heart failure in the subject or at least representative of an increased risk of heart failure. Thus, a significant reduction in the relative time parameter as trended over time corresponds to an earlier onset of ventricular filling in the heart cycle, which is indicative of heart failure. The detectable movement of the ventricular filling to an ever earlier time position in the heart cycle is detectable at a much earlier heart failure progression stage than the conventional ejection-fraction based heart failure parameters. As a consequence, a heart failing subject can be diagnosed before the disease has progressed to a late stage and compensating actions can be initiated to combat the heart failure, thereby increasing the chances of successful treatment.

The present invention also relates to a method of diagnosing heart failure in the subject based on the relative time parameter for the onset of ventricular filling.

BRIEF DESCRIPTION OF THE DRAWINGS

FIG. 9 is a flow diagram illustrating a method of diagnosing heart failure according to the present invention.

FIG. 11 is a flow diagram illustrating additional steps of the heart failure diagnosing method.

FIG. 12 is a flow diagram illustrating additional steps of the heart failure diagnosing method.

DESCRIPTION OF THE PREFERRED EMBODIMENTS

Figure 6:
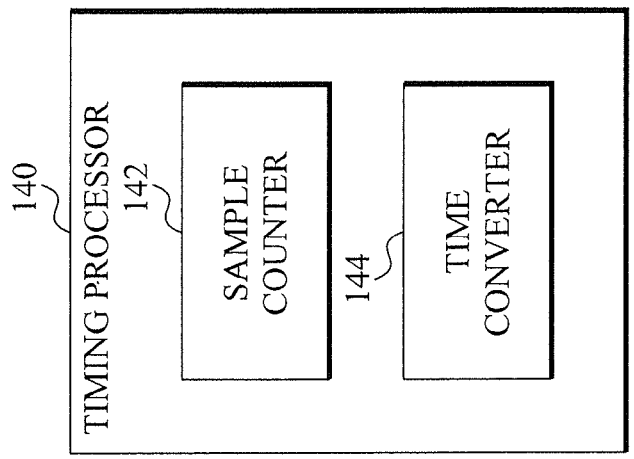
FIG. 6 is a schematic block diagram of a timing processor according to an embodiment of the present invention.

Throughout the drawings, the same reference characters will be used for corresponding or similar elements.

The present invention relates to implantable medical devices and methods having capability of detecting heart failure of an animal subject, preferably mammalian subject and more preferably a human subject, at a very early state of the heart failure progression. The invention uses a radically different approach than taken by the prior art ejection-fraction based detection techniques to achieve this early detection.

The invention is based on the effect that, following a subject's falling ill with heart failure and during the heart failure progression, the subject body and in particular the heart endeavors to compensate for the condition. This compensation involves increasing the time spent for mechanically filling of the ventricles during a heart cycle. The reason for this is to allow sufficient filling time to thereby increase the pre-load. According to Starling's law, an increased pre-load in turn yields an increase in the stroke volume of the heart.

The present invention therefore monitors onset of ventricular filling and diagnosis any heart failure condition based on a detected change in the timing of the ventricular filling in a heart cycle.

Figure 1:
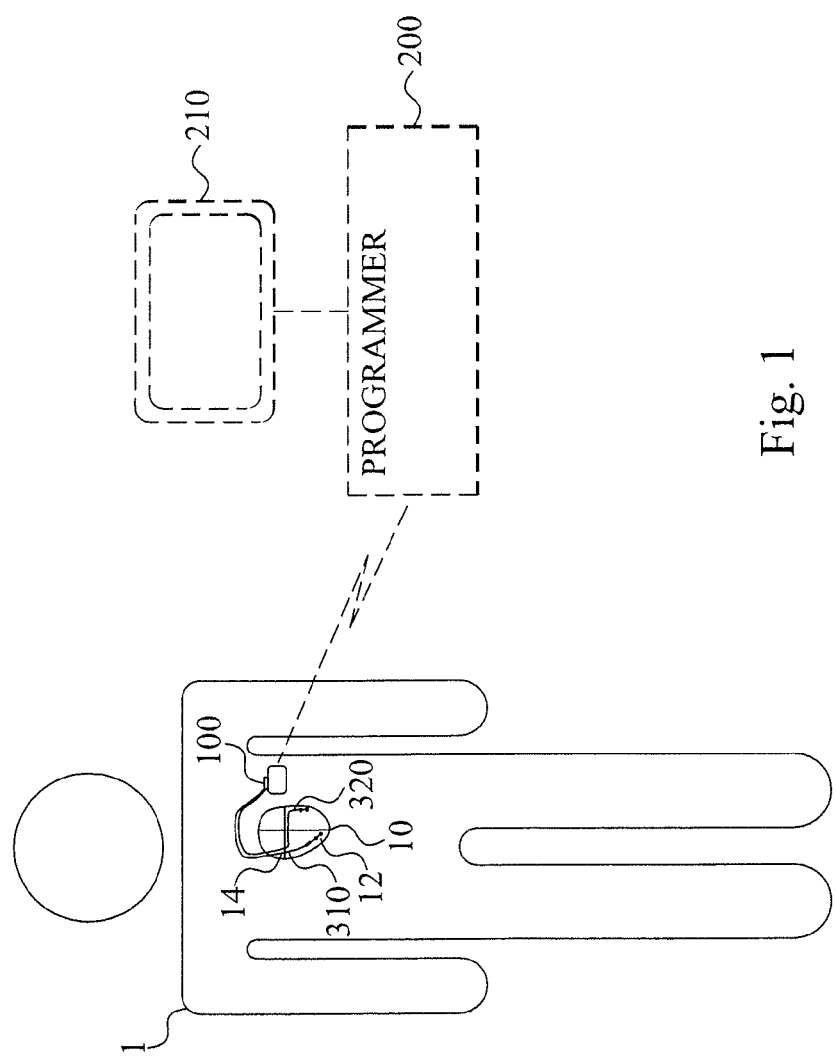
FIG. 1 is a schematic overview of a subject having an implantable medical device according to the present invention.

FIG. 1 is a schematic overview of a patient 1 having an implantable medical device, IMD, 100 according to the present invention. In FIG. 1, the IMD 100 is illustrated as a device that monitors and/or provides therapy to the heart 10 of the patient 1, such as a pacemaker, cardiac defibrillator or cardioverter. The IMD 100 is, in operation, connected to one or more, two in the figure, intracardiac leads 310, 320 inserted into different heart chambers, the right and left ventricles 12 in FIG. 1. The present invention is though not limited to ventricular leads 310, 320 but can also be used in connection with leads positioned in the right or left atrium 14 of the heart 10. Actually, also non-intracardiac leads, including epicardiac leads can also be used.

FIG. 1 also illustrates an external programmer or clinician's workstation 200 that can communicate with the IMD 100. As is well known in the art, such a programmer 200 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the programmer 200 before display to a clinician on a connected display screen 210. In the light of the present invention, such diagnostic data can include heart failure data descriptive of a heart failure status or risk of the patient 1 determined by the IMD 100 and/or other diagnostic data relating to the heart failure detection and/or classification.

Figures 2, 3, 7:
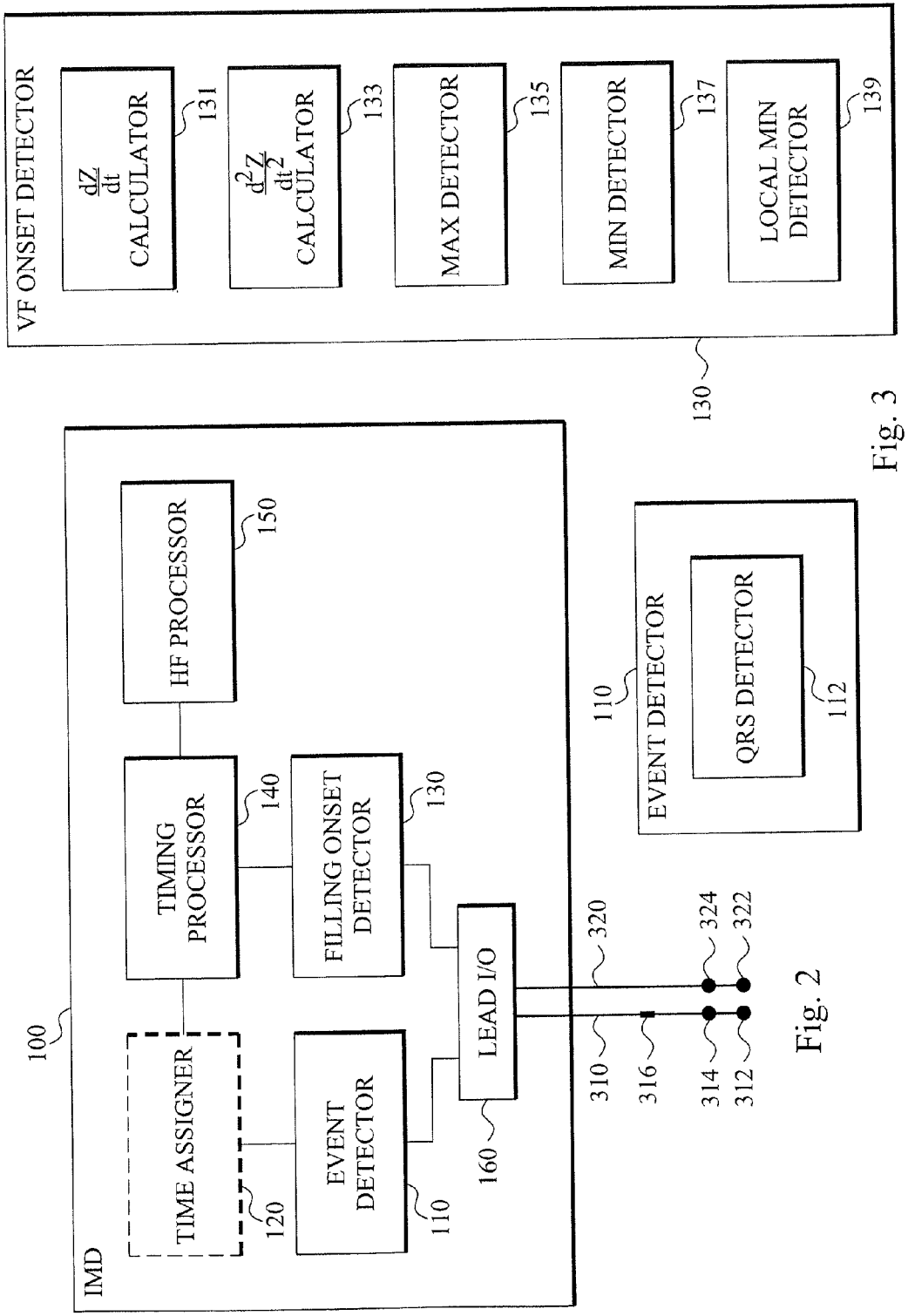
FIG. 2 is a schematic block diagram of an implantable medical device according to an embodiment of the present invention.
FIG. 3 is a schematic block diagram of an event detector according to an embodiment of the present invention.
FIG. 7 is a schematic block diagram of a ventricular filling onset detector according to an embodiment of the present invention.

FIG. 2 is a schematic block diagram of an IMD 100 according to the present invention. The IMD 100 comprises an event detector 110 for detecting occurrence of a predefined heart event during a detecting time window in connection with onset of a heart cycle.

The time window employed according to the present invention starts from the onset of the heart cycle and runs up to and including the opening of the aortic valves. The start of the heart cycle is preferably regarded as the occurrence a pre-defined electrical event, such as the depolarization of the atriums or ventricles. In a preferred embodiment of the invention, a heart cycle is defined as the time period between two consecutive QRS complexes (depolarization of the ventricles), typically denoted an RR interval in the art. However, in an alternative embodiment, the heart cycle could be defined as the time period between two consecutive P waves (depolarization of the atriums).

There are several different well-defined heart events that consistently occur in the respective detection time window of different heart cycles. Any of these events can be detected by the event detector 110 of the present invention. A preferred such event is the occurrence of the QRS complex in the detection time window. In such a case, the event detector 110 can be implemented according to FIG. 3 having a QRS detector 112. The QRS detector 112 is connected to a lead input and output (I/O) of the IMD 100. This lead I/O 160 is in turn connectable to one or more cardiac leads 310, 320, preferably intracardiac leads 310, 320. These leads 310, 320 each comprises one or more electrodes 312, 314, 316; 322, 324 for sensing and measuring different electrical parameters in the subject's heart and/or applying electrical pulses or shocks to the heart. In this context different forms of lead electrodes well-known in the art can be used, including lead tip electrodes 312, 322, lead ring electrodes 314, 324 and lead coil electrodes 316. The electrodes 312, 314, 316; 322, 324 preferably measure intracardiac electrical signals that are forwarded through the leads 310, 320 and lead input 140 to the QRS detector 112 for processing. The detector 112 then uses these intracardiac electric signals for detecting the presence of a QRS complex in a heart cycle. These electric signals preferably represent electrocardiogram (ECG) signals and preferably an intracardiac electrocardiogram (IEGM) signals.

It is though anticipated by the present invention that other signals besides ECG an IEGM signals can be used by the QRS detector 112 for QRS detection. For instance, it is possible to identify a QRS event in a (cardiogenic) impedance signal determined by the IMD 100. In such a case, the IDM 100 includes, as is further described herein, functionality for determining such an impedance signal. The QRS detector 112 processes the impedance and identifies the QRS event therein.

An alternative implementation of the event detector 110 is arranged for detecting the closure of the mitral valve (left atrioventricular valve) of the heart. In such a case, the event detector 110 can include or may be connectable to an implantable pressure sensor, such as connected to one of the cardiac leads 310, 320 or present on a dedicated pressure probe. The closure of the mitral valve is registered as a pressure change in a recorded pressure sensor. The pressure sensor is preferably implanted in the left ventricle. Generally, the left ventricle pressure increases significantly immediately following the mitral vale closure and the start of this pressure increase can be registered by the pressure sensor.

Instead of including or being connected to a pressure sensor, the event detector 110 can include or be connected to an acoustic sensor present on one of the leads 310, 320 or on a separate acoustic probe. The acoustic sensor registers acoustic data originating from the heart. This data is being processed by the event detector 110 for the purpose of generating a phonocardiogram (PCG). The closure of the mitral valve can easily be detected as the second component of the first one of the PCG from a heart cycle.

The acoustic sensor or pressure sensor can alternatively be employed by the event detector 110 for detecting another predefined cardiac event in the detection time window. This other event is the opening of the aortic valves, which also defines the end of the detection window. However, as is known in the art, valve openings can be somewhat more difficult to effectively detect with an acoustic sensor as compared to a valve closure. As a consequence, the opening of the aortic valves is preferably detected through pressure measurements rather than acoustic measurements.

A further predefined heart event that can be used according to the present invention and detected by the event detector 110 is the onset of ventricular emptying, which coincidence with the opening of the aortic valves. The blood emptying from the ventricles can advantageously be detected from cardiogenic impedance data.

Thus, there are several different cardiogenic events occurring in the detection time window following the start of a heart cycle that can be used according to the present invention. The event detector 110 marks or notifies the sample in the relevant signal, such as impedance signal, IEGM signal, ECG signal, PCG signal, pressure signal, which corresponds to the detected cardiogenic event.

An optional time assigner 120 is preferably implemented in the IMD 100 connected to the event detector 110. This assigner 120 is arranged for assigning a time reference to the heart event detected by the event detector 110. In a preferred embodiment, the time assigner 120 assigns the time reference to the sample number identified by the event detector 110 and coinciding in time with the detected event. The assigner 120 preferably sets the time of the detected event (identified sample) as a zero time, $t_{HE}=0$, where $t_{HE}$ represents the time assigned to the detected heart event sample.

An onset detector 130 of the IMD 100 is implemented for detecting the onset of ventricular filling of the heart in the heart cycle. This ventricular filling is the heart cycle phase, in which blood enters the ventricles from the atriums and therefore occurs following the isovolumetric relaxation of the heart.

According to the present invention the actual timing of the onset of ventricular filling in a heart cycle is an efficient and very early indication of a heart failure condition of the subject. As a consequence, the IMD 100 including a timing processor 140 connected to the onset detector 130 for determining a relative time of the detected ventricular filling onset. This relative time is determined based on the time reference assigned by the time assigner 120. As a consequence, the timing processor 140 preferably determines the ventricular filling time relative the time assigned to the detected predefined heart event.

FIG. 6 illustrates a preferred implementation of the timing processor 140 of the present invention. The processor 140 includes a sample counter 142 arranged for counting samples in the signal processed by the onset detector for the purpose of detecting ventricular filling onset. The counter 142 counts the number of samples occurring between the sample coinciding in time with the detected pre-defined heart event and the sample coinciding in time with the detected onset of ventricular filling. Thus, assume that $s_{HE}$ represents the heart event sample and $s_{HF}$ denotes the ventricular filling sample. In such a case, the sample counter 142 calculates $N_{HF}=s_{HF}-s_{HE}$.

A time converter 144 of the timing processor 140 uses this determined number of samples $N_{HF}$ for determining the relative time of the detected onset of ventricular filling. The converter 144 divides the number of samples with the sampling frequency $f_s$ of the signal employed by the onset detector 130 for detecting the ventricular filling event. Thus, the relative time $t_{HF}$ of the onset of ventricular filling is determined as $$t_{HF} = \frac{N_{HF}}{f_s} - t_{HE}$$

and preferably $$t_{HF} = \frac{N_{HF}}{f_s}$$

if $t_{HE}=0$.

A heart failure processor 150 of the IMD 100 uses the relative time determined by the timing processor 140 for generating detection data indicative of the heart failure risk or status of the subject. Thus, the determined time for the onset of ventricular filling relative the (fixed) pre-defined heart event in the heart cycle is representative of the heart failure status of the subject and is of high diagnostic value for detecting an occurrence and progression of heart failure.

In a preferred embodiment, the timing processor 140 determines the relative time at multiple different time instances for the subject. In such a case, the heart failure processor 150 can use multiple such time values for trending purposes and detecting an occurrence of heart failure based on a change (decrease) in the determined time parameter.

The units 110 to 160 of the IMD 100 may be provided as hardware, software or a combination of hardware and software. In the figure only those IMD units 110 to 160 directly involved in the present invention have been indicated. It is anticipated by the present invention that the IMD 100 also comprises other units and functionalities directed to its operation but not directly involved in the invention. The units 112, 142 and 144 of the event detector 110 and the timing processor 140 may also be implemented in hardware, software or a combination of hardware and software. In an alternative implementation, at least one of the units 112, 142 and 144 are provided elsewhere in the IMD 100.

Figure 4:
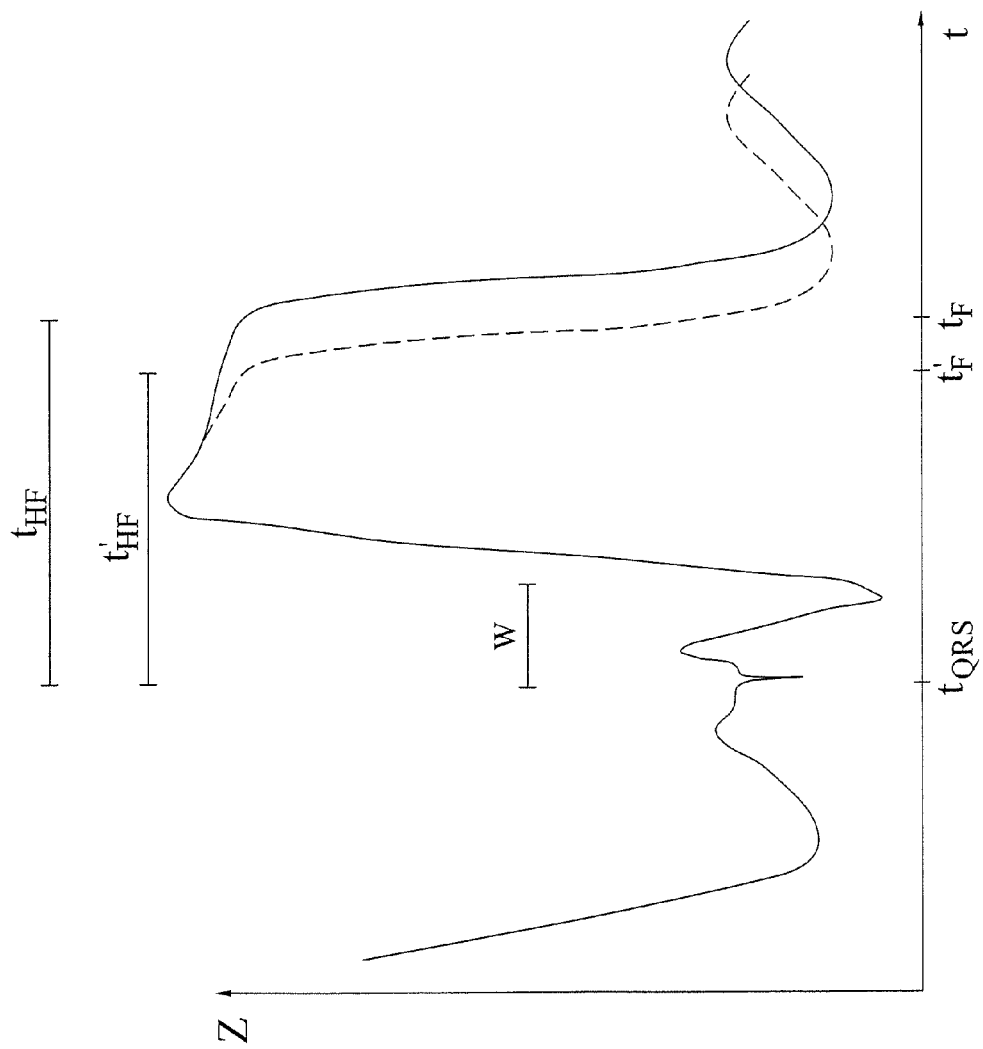
FIG. 4 is a diagram illustrating a change in impedance signal in connection with an early heart failure indication detectable according to the present invention.

FIG. 4 is a diagram illustrating a signal determined by the IMD over a heart cycle, in this case in the form of an impedance signal. The figure illustrates a possible implementation of the detection time window W. In this case, the start of the heart cycle is regarded as the QRS complex. The time window W therefore extends from the QRS complex up to the opening of the aortic valves and the ventricular emptying, detectable as a local maximum in the second derivative of the impedance data following the local minimum in the impedance signal after the QRS.

The continuous line in the figure corresponds to the cardiogenic impedance of a healthy subject during a heart cycle. The time for onset of ventricular filling $t_F$; occurs following the almost constant plateau in the impedance signal corresponding to isovolumetric relaxation (the plateau has though in practice slightly sloping form due to geometrical changes of the heart during the relaxation). The relevant heart failure parameter of the present invention is the relative time between the onset of the ventricular filling and the pre-defined heart event, in this case the QRS complex.

The dashed line illustrates the corresponding impedance signal for a subject suffering from heart failure. As is seen by comparing this line with the continuous line, the onset of ventricular filling has been moved to an early stage of the heart cycle. This is clearly evident by comparing the relative times $t_{HF}$, $t'_{HF}$ to see that $t'_{HF}=t'_F-t_{QRS}<t_F-t_{QRS}=t_{HF}$. The relative timing of onset of ventricular filling in a heart cycle is therefore a very good heart failure status parameter.

Figure 5:
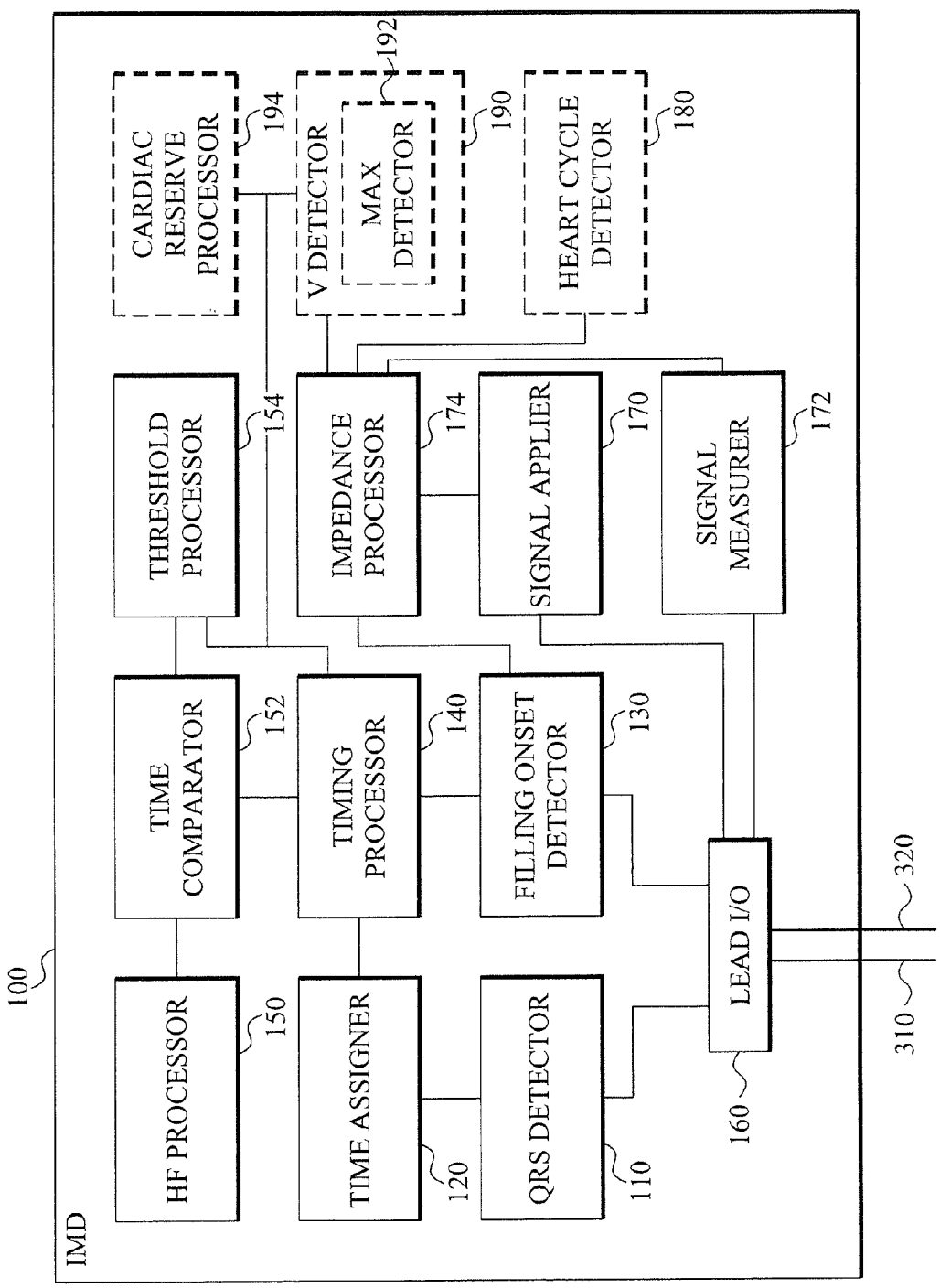
FIG. 5 is a schematic block diagram of an implantable medical device according to another embodiment of the present invention.

FIG. 5 is a schematic block diagram of another embodiment of the IMD 100. The IMD 100 comprises, in addition to the units disclosed in FIG. 2, a signal applier 170 for applying, over two electrodes of the lead(s) 310, 320 connectable to lead input 160 of the IMD 100, an electrical signal to the blood present in the measuring cavity. The signal applier 170 can be arranged for generating and applying a predefined current or voltage signal. As is known in the art, such an applied current or voltage signal, preferably current signal can be a stepwise or gradually changing (current) signal.

A signal measurer 172 is implemented in the IMD 100 for measuring, using at least two electrodes of the lead(s) 310, 320 connectable to the lead input 160 of the IMD 100, a resulting electrical signal over at least a portion of the heart. This measurer 172 preferably measures a resulting voltage signal, if the signal applier 170 applied a current signal or pulse, and measures a resulting current signal, if the applier 172 applied a voltage signal.

As is well known in the art, there are different impedance vectors that can be used, including bipolar, tripolar and quadropolar vectors. In bipolar impedance determination, the same two electrodes are used for both signal application and signal measuring. A tripolar vector is obtained if one of the signal applying electrodes is also employed in the resulting signal measurement. Finally, quadropolar measurements use dedicated signal applying and dedicated signal measuring electrodes. In a preferred embodiment of the present invention, the impedance signal is preferably determined through quadropolar measurements as these best reflects volume changes in the heart ventricles and in particular the left ventricle.

Depending on which types of leads 310, 320 that are connected to the IMD 100, different electrodes can be used in the quadropolar configuration. A preferred embodiment of the invention uses a left ventricular (LV) lead 310 and a right ventricular (RV) lead 320. In such a case, a current signal can be applied between the RV and LV ring electrodes, while a resulting voltage is sensed between the RV and LV tip electrodes. Other examples include apply current between RV and LV tip electrodes, RV ring and LV tip electrodes or RV tip and LV ring electrodes with the measurement between RV and LV ring electrodes, RV tip and LV ring electrodes or RV ring and LV tip electrodes.

The IMD 100 also comprises an impedance processor 174 for determining an impedance signal or data based on the electrical signal applied by the signal applier 170 and the resulting electrical signal measured by the signal measurer 172. The impedance processor 174 employs well known signal processing techniques for determining the impedance data based on the raw input electrical signals. Briefly, the input measured AC voltage is optionally pre-amplified and an integrated by calculating the voltage area of the signal per pulse. The applied AC current signal is also integrated by calculating the current area of the signal per pulse. The integrated absolute impedance can then be calculated as the quotient between the voltage area and the current area. This raw impedance signal may be further processed in a filter chain. The filter output is A/D converted to form the desired output impedance signal.

The impedance signal of the present invention can be the "raw" impedance signal obtained by following the processing discussed above. Alternatively, further filtering of the "raw" signal can be used to obtain a cardiogenic impedance signal reflecting the cardiogenic contribution to the impedance changes and thereby reducing the impedance contribution from other sources, such as respiration.

The onset detector 130 of the IMD 100 processes the impedance processor 174 for the purpose of detecting the onset of ventricular filling. In the following, the detection of onset of ventricular filling is discussed further and exemplified by processing of impedance data. However, the present invention is not limited to usage of impedance signals for detecting this ventricular filling. In clear contrast, other cardiogenic signals can be employed the IMD 100 for the filling detection. Examples of such other signals include pressure signal collected by an implantable pressure sensor provided on one of the medical leads 310, 320 or a dedicated pressure probe connected to the IMD 100. There are several implantable pressure sensors available in the art that can be used according to the present invention. Non-limiting example includes microelectromechanical system (MEMS) based pressure sensors.

The left ventricular pressure can be recorded and analyzed for identifying the onset of ventricular filling according to the invention by a pressure sensor arranged in connection with or preferably in the left ventricle. In such a case, the onset of ventricular filling follows the top in the pressure signal that occurs from the closure of the mistral valve to the ventricular filling. Thus, the point in the pressure signal corresponding to the end pressure top or spike and when the pressure reaches baseline levels can easily be identified and used as indication of start of the ventricular filling.

Oxygen data, such as mixed venous oxygen ($SvO_2$) can alternatively be used by the IMD for detection of onset of ventricular filling. Implantable $SvO_2$ sensors are available in the art, including integrated into IMD leads 310, 320. These oximetry sensors are often of optical nature. For instance red and light-emitting diodes can be used, while measuring the reflectance of the light from each diode by a photodetector. The relative reflectance ratio is proportional to the ventricular $SvO_2$.

The $SvO_2$ is advantageously implanted in connection with or in the left ventricle. In such a case, the sensor would detect the oxygen increase as oxygenated blood from the lungs return and fill the ventricle. The point in time corresponding to the start of this oxygen increase coincides with onset of ventricular filling.

Thus, even though impedance measurements are preferred for implementation of the present invention due to the easy at which ventricular filling onset can be detected and the relaxed need for dedicating sensor equipment, other parameters as illustrated above can be used by the onset detector 130 of the invention.

Figure 8:
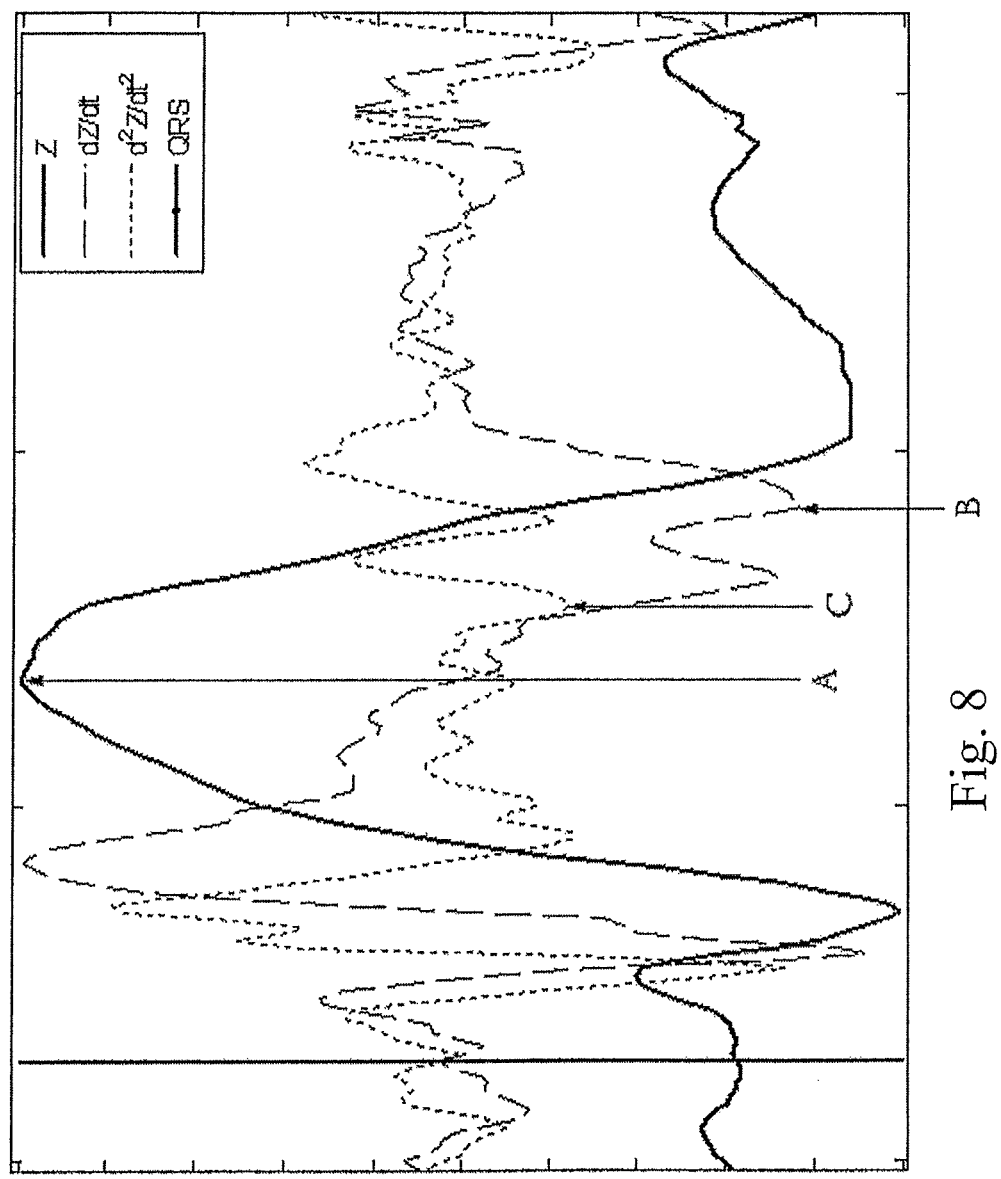
FIG. 8 is a diagram illustrating calculation of time data according to a particular embodiment of the present invention.

With reference to FIGS. 7 and 8, a preferred embodiment of the onset detector 130 will be discussed in more detail. The detector 130 comprises a first derivative calculator 131 for calculating a first time derivative of the impedance signal. A second derivative calculator 133 calculates a second time derivative of the impedance signal. FIG. 8 illustrates the impedance signal together with its first and second time derivatives over at least a heart cycle.

A maximum detector 135 of the onset detector 130 is arranged for identifying a global maximum of the impedance signal during the heart cycle. This detector 135 can simply parse through all impedance samples determined for the heart cycle and notifying the sample number of the sample having the largest (positive) impedance value. This corresponds to point A in FIG. 8 and coincides with the end of ventricular emptying.

The detector 130 also includes a minimum detector 135 implemented for detecting a minimum of the first derivative signal during the heart cycle following the detected maximum in the impedance signal. Thus, the sample of the first time derivative coinciding in time with the identified global maximum impedance sample is identified. The derivative samples are then investigated in sample/time order until the minimum value is reached in the heart cycle. As is illustrated in FIG. 8, this minimum value is the smallest minimum of the first derivative following the time of the maximum in the impedance signal. Point B indicates this minimum first derivative impedance value. The sample number of the minimum derivative value is notified.

A local minimum detector 139 is provided for detecting a smallest local minimum of the second derivative of the impedance preceding the detecting minimum in the first derivative signal during the heart cycle but following the maximum in the impedance signal. Thus, the detector 139 starts at the second derivative sample coinciding in time with the detected minimum first derivative value. The detector 139 then parses the second derivative samples backwards in time up to the sample coinciding in time with the detected maximum impedance value. In such a case, the sample corresponding to the smallest second derivative value indicates the smallest local minimum in this period and yields point C in FIG. 8. This point C corresponds to the point in time of the onset of ventricular filling.

In a particular embodiment, the onset detector 130 identifies the sample in the impedance signal coinciding in time with the identified point C. The timing processor of the IMD can then calculate the difference between the sample number for the identified ventricular filling sample in the impedance signal and the impedance sample corresponding to the QRS complex. Dividing this difference with the sampling frequency for the impedance signal yields the relative time for the onset of ventricular sampling for the current heart cycle.

The units 131 to 139 of the onset detector 130 may be provided as hardware, software or a combination of hardware and software. A distributed implementation is also possible where at least one of the units 131 to 139 is implemented elsewhere in the IMD.

In a preferred embodiment, the signal applier 170 of the IMD 100 applies the current or voltage signal during at least one, preferably multiple, i.e. at least two, consecutive respiratory cycles of the subject. The signal measurer 172 senses the resulting voltage or current signal and the impedance processor 174 determines the impedance signal for, preferably, the complete respiratory cycle(s).

In such a case, the impedance processor 174 identifies multiple different heart cycles in the impedance signal. The M impedance signals over these M identified heart cycles are then averaged to get rid of noise and respiration artifacts. The result is an averaged impedance signal covering the time period of a complete heart cycle.

In an alternative embodiment for reducing the noise and respiration artifacts is to utilize a heart cycle detector 180 of the IMD 100. This cycle detector 180 processes the impedance signal recorded over multiple respiratory cycles. The detector 180 detects those heart cycles occurring at a predefined respiratory phase in the impedance signal. For instance, the cycle detector 180 could identify those heart beats which took place after expiration and before the next consecutive inhalation. This will yield a subset of heart cycles which are all recorded during more similar conditions. The impedance processor 174 then determines an average impedance signal based on the heart cycle subset.

The IMD 100 preferably includes a time comparator 152 implemented for comparing the relative time parameter determined by the timing processor with a time threshold. In such a case, a significant difference between the time parameter and the threshold is indicative of the presence of heart failure or at least an increased risk for heart failure. This means that the heart failure processor 150 is arranged for generating the heart failure detection data based on the parameter-threshold comparison.

The time comparator 152 can for instance compare the time parameter with the threshold and if the threshold exceeds the parameter, the processor 150 generates detection data indicative of heart failure for the subject. Alternatively, the time comparator 152 can calculate a quotient between the time parameter and the threshold. In such a case, a quotient smaller than one (or larger than one for a quotient between threshold and the time parameter) indicates the presence of heart failure.

The IMD 100 preferably includes a threshold processor 154 implemented for determining the time threshold employed by the time comparator 152. In a preferred embodiment, the threshold is determined based on a relative time of a detected ventricular filling onset previously determined by the timing processor 140. Thus, the threshold is determined based on previously determined timing data relating to past heart cycles when the subject's heart did not suffer from any heart failure condition.

This previous relative time determination is preferably performed during similar conditions as a current determination of timing data. This can be realized by having a number of conditions that should be met for conducting a measurement according to the present invention. Examples of such conditions could be to perform the event detection, ventricular filling detection and relative time determination during night time, when it is expected that the subject is resting. In such a case, the IMD 100 comprises a clock unit triggering timing data determination during a predefined time period of day, such as sometimes between 1 a.m. and 5 a.m.

Alternatively, or in addition, the data determination is performed during a rest mode of the IMD 100. This means that the IMD 100, such a pacemaker or ICD, should be in a rest mode when measuring and determining the relevant timing data.

A further example condition could be the heart rate of the subject's heart. The IMD 100 then includes a rate determining unit connected to the lead I/O unit 160 and implemented for estimating a current heart rate based on electrical signals sensed from the heart. In such a case, determination of timing data could be performed if the heart rate indicates a resting state, such as having a rate below 75 beats per minute for instance.

It is expected by the present invention that the above listed example conditions could be used in combination, in such case the measurements of the present invention are performed during night time when the IMD 100 is in rest mode and the subject has a resting heart rate.

In a preferred embodiment, the threshold processor 154 not only determines a threshold time value but is preferably also implemented for periodically, intermittently or at given time instances update the threshold value. In such a case, the threshold updating can be implemented for updating the threshold value based on newly determined timing data if the threshold does not significantly exceed the timing data. This means that the threshold is determined as a (weighted) average of the previous threshold value and the determined relative time.

In addition to detecting a heart rate condition or increased risk for heart rate condition, the IMD 100 can furthermore determine a cardiac reserve of the heart. This cardiac reserve corresponds to the heart's ability to respond to demands that exceed ordinary circumstances. The cardiac reserve measure is indicative of the severity of the detected heart failure and can be used as an indication of the progression of the heart disease for the subject.

The IMD 100 therefore preferably includes a volume detector 190 arranged for detecting occurrence of a minimum blood volume in a ventricle, preferably left ventricle, of the heart during a heart cycle. There are several different measurement techniques that can be used for the purpose of estimating blood volumes and monitoring blood volume changes in the ventricle. In a preferred implementation, the volume detector 190 includes a maximum detector 192 arranged for detecting a maximum in the impedance signal during a heart cycle. The impedance signal is determined by the impedance processor 174 as previously discussed. The maximum detector 192 then parses through the impedance samples corresponding to a heart cycle in order to identify the one having the largest value.

The timing processor 140 determines a relative time of the detected minimum blood volume based on the assigned time reference of the detected predefined cardiac event. In a preferred embodiment, the processor 140 determines the difference between sample numbers of the sample coinciding with maximum impedance (minimum blood volume) and the sample coinciding with the predefined cardiac event. The difference is then divided by the sample frequency for the impedance signal to get the relative time of the minimum blood volume.

A cardiac reserve processor 194 processes the determined relative time from the timing processor 140 and generates detection data indicative of a cardiac reserve of the heart based on the relative time of the detected minimum blood volume and the relative time of the onset of ventricular filling. In a particular embodiment, a difference between or a quotient of the two relative times is calculated and used as cardiac reserve parameter.

The parameter can then be compared to a threshold value, such as a previously determined cardiac reserve parameter determined when the subject is diagnosed as not suffering from heart failure. Generally, the smaller the difference between the two relative time values the smaller the cardiac reserve and the longer the heart failure has progressed.

The diagnostic data determined according to the present invention, such as relative time of onset of ventricular filling and optionally relative time of detected minimum blood volume in ventricular, can be stored in a memory provided in the IMD 100. The data can alternatively, or in addition, be uploaded to an external communications unit, such as programmer, using a wireless transmitter and antenna unit of the IMD 100 according to techniques well-known in the art.

The units 110 to 194 of the IMD 100 may be provided as hardware, software or a combination of hardware and software. In the figure only those IMD units 110 to 194 directly involved in the present invention have been indicated. It is expected by the present invention that the IMD 100 also comprises other units and functionalities directed to its operation but not directly involved in the invention.

FIG. 9 is a flow diagram illustrating a heart failure diagnosing method according to the present invention. The method starts in step S1, which detects occurrence of a predefined cardiac event in a detection time window from start of a heart cycle up to opening of aortic valves in said heart cycle as previously described. The predefined cardiac event is advantageously a QRS complex. A next step S2 assigns a time reference to the detected cardiac event. This time reference can, for simplicity, be a zero time.

Onset of ventricular filling of a heart in a subject during the heart cycle is detected in step S3. The relative time for this detected filling onset is determined in step S4 based on the time reference assigned in step S2. This relative time is then used in step S5 as diagnostic parameter for the purpose of detecting a heart failure or increased risk for heart failure in the subject.

As has been discussed in the foregoing, the diagnosis of the method is preferably performed at multiple different time instances, such as periodically at a predefined periodicity, such as 4-10 times per day.

Figure 10:
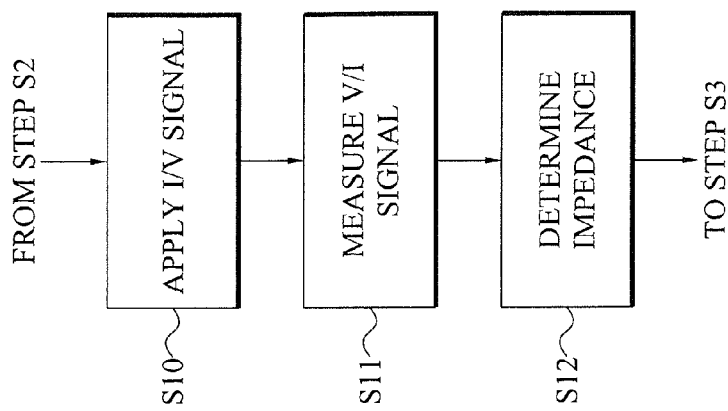
FIG. 10 is a flow diagram illustrating additional steps of the heart failure diagnosing method.

FIG. 10 is a flow diagram illustrating additional steps of the diagnosing method of FIG. 9. The method continues from step S2 of FIG. 9. Step S10 involves applying a current or voltage signal using two electrodes to at least a portion of the subject's heart. Two electrodes are correspondingly used in step S11 for sensing or capturing the resulting voltage or current signal. An impedance signal is then determined based on the sensed voltage (current) signal and based on information of the applied current (voltage) signal in step S12. The method then continues to step S3 of FIG. 9, where the onset of ventricular filling is determined based on the impedance signal.

In a preferred embodiment, multiple consecutive heart cycles are monitored for the purpose of determining the relative onset time parameter. For instance, the impedance signal determined in step S12 of FIG. 10 can be recorded over multiple heart cycles occurring during one or more respiratory cycles. The signal over these multiple cycles can then be co-processed as disclosed in FIG. 11 or FIG. 12 in order to reduce noise and respiratory contribution in the signal.

FIG. 11 illustrates additional impedance signal processing and continues from step S12 of FIG. 10. A next step S20 identifies the respective portions of the impedance signal corresponding to different heart cycles. The signals at these heart cycles are then averaged in step S21 to get an average impedance signal. The method continues to step S3 of FIG. 9, where the onset of ventricular filling is detected based on the average impedance signal.

If the method instead is conducted according to FIG. 12, it continues from step S12 of FIG. 9. A next step S30 identifies a predefined phase in the respiratory cycle. Those heart cycles coinciding with the identified respiratory phase in different respiratory cycles are identified in step S31. Step S32 calculates an average impedance of the identified heart cycle from step S31. This method typically involves performing the averaging over fewer heart cycles as compared to FIG. 11 unless the impedance signal is recorded over a comparatively longer. However, by synchronizing the relevant impedance signal to a particular phase of the respiratory cycle, the respiratory contribution to the impedance signal can be minimized.

An alternative or additional approach is to filter the impedance signal as mentioned above to mainly get the cardiogenic contribution and suppress the impact from respiration.

Figure 13:
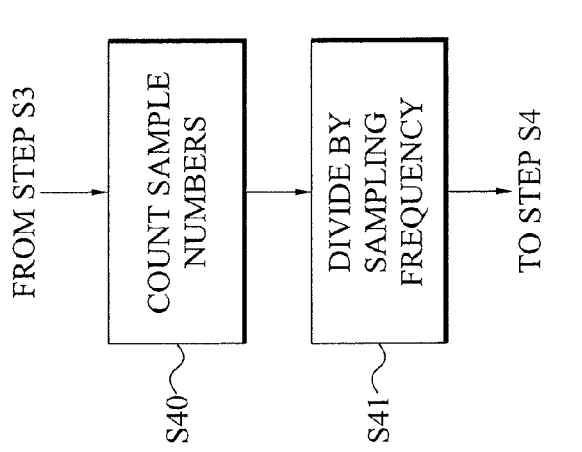
FIG. 13 is a flow diagram illustrating additional steps of the heart failure diagnosing method.

FIG. 13 is a flow diagram illustrating additional steps of the diagnosing method. The method continues from step S3 of FIG. 9. A next step S40 counts the number of samples in the impedance signal from the sample coinciding in time with the detected cardiac event to the sample coinciding in time with the detected onset of ventricular filling. This number is divided by the impedance sampling frequency in step S41. The relative onset time is then obtained directly from the quotient or is determined therefrom in step S4 of FIG. 9.

Figure 14:
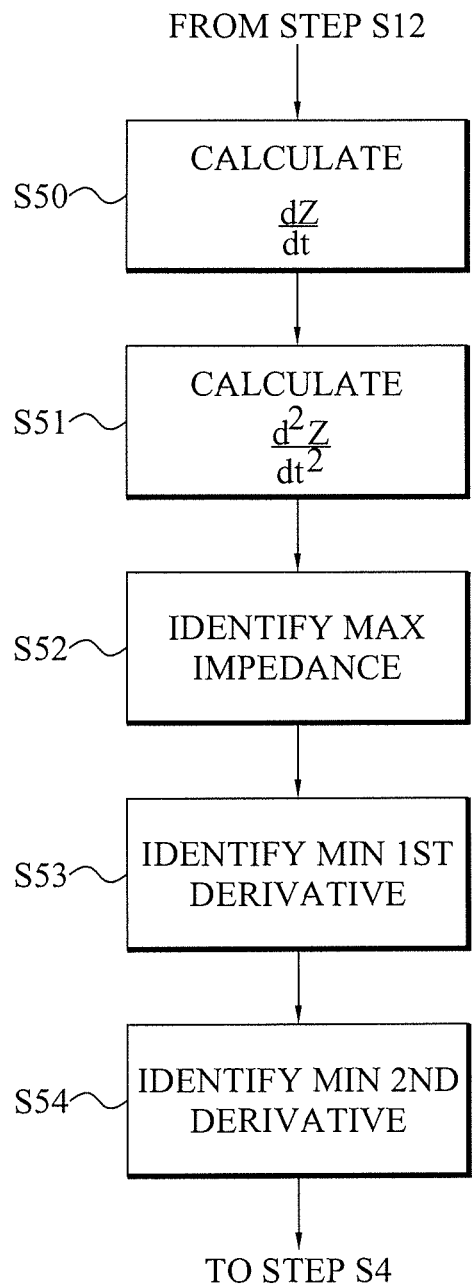
FIG. 14 is a flow diagram illustrating additional steps of the heart failure diagnosing method.

FIG. 14 is a flow diagram illustrating additional steps of the diagnosing method. The method continues from step S12 of FIG. 10. The first time derivative of the impedance signal is determined in step S50 and the second time derivative is determined in step S51.

The (average) impedance signal during a heart cycle is parsed to detect a global maximum of the impedance for the heart cycle in step S53. The sample or relative time of this identified maximum impedance is notified. A next step S53 identifies a minimum of the first derivative of the impedance signal occurring during the heart cycle but after the maximum identified in step S52. The minimum is preferably the smallest first derivative value occurring in the first time derivative signal after the time corresponding to the maximum in the impedance signal. The sample or relative time coinciding with the identified minimum first derivative is notified.

The second time derivative signal is then parsed in the window extending from the time of the maximum in the impedance signal identified in step S52 and the minimum in the first time derivative identified in step S53. The smallest minimum of the second time derivative in this parsing window is identified in step S54. The sample or relative time coinciding with this identified minimum in the second time derivative is indicative of the onset of ventricular filling. The method continues to step S4 of FIG. 9, where the relative time of filling onset is determined based on the minimum identified in step S54.

Figure 15:
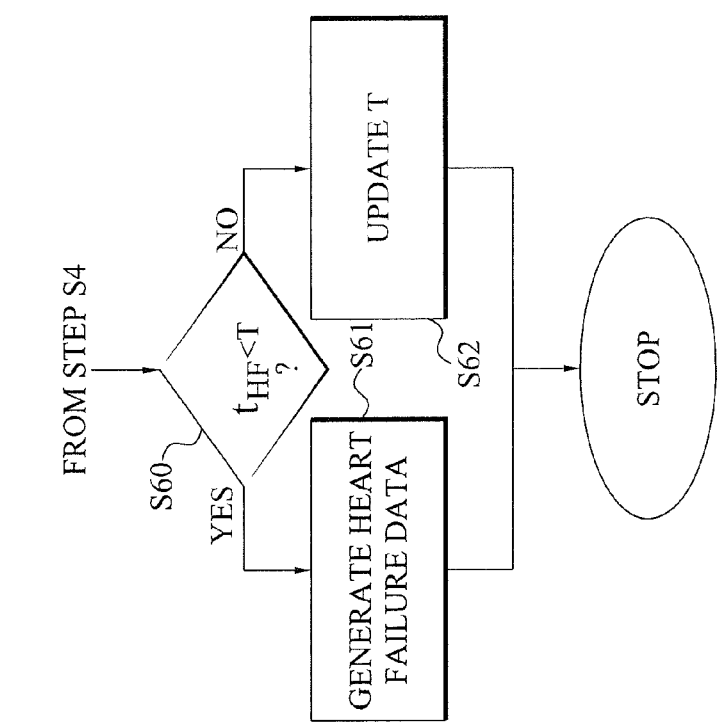
FIG. 15 is a flow diagram illustrating an embodiment of the heart failure detecting step in FIG. 9 in more detail.

FIG. 15 is a flow diagram illustrating a possible implementation of the heart failure detecting step of FIG. 9. The method continues from step S4 of FIG. 9. A next step S60 compares the determined relative time of filling onset with a threshold time. If the relative time is lower then the threshold time, there is an increased risk for heart failure and data indicative of this diagnosed heart failure (risk) is generated in step S61. However, if the relative time is not significantly smaller than the threshold, no heart failure is detected and the method continues to the optional step S62, where the threshold value T is updated based on the previous threshold value $T_p$ and the determined relative time $T_{HF}$, $T=f(T_p,t_{HF})$ and preferably $T=wT_p+(1-w)t_{HF}$ where $0<w<1$.

Figure 16:
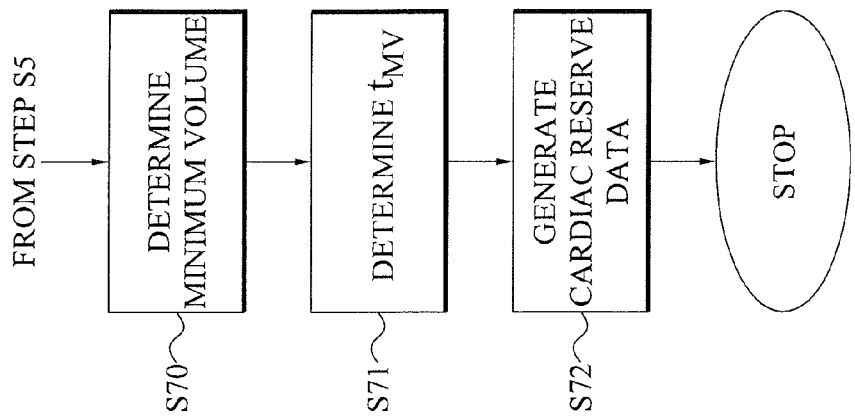
FIG. 16 is a flow diagram illustrating additional steps of the heart failure diagnosing method.

FIG. 16 illustrates a flow diagram of additional steps of the conditioning method for estimating a cardiac reserve of the subject's heart and getting an indication of the heart failure progression. The method continues from step S5 of FIG. 9. A next step S70 detects the occurrence of a minimum blood volume in a ventricle of the heart during a tested heart cycle. This minimum volume is preferably identified as a maximum in the impedance signal during the heart cycle. The relative time $t_{MV}$ of the detected minimum blood volume is determined in step S71 based on the assigned time reference of the predefined cardiac event. A cardiac reserve parameter is then determined in step S72 based on the relative time $t_{MV}$, and the relative time $t_{HF}$ of filling onset from step S4 of FIG. 9. In a preferred embodiment, a reduction in cardiac reserve and therefore a progression of the heart failure is indicated by a reduction in the difference $t_{HF}-t_{MV}$, or an increase of the quotient $$\frac{t_{MV}}{t_{HF}}.$$

Although modifications and changes may be suggested by those skilled in the art, it is the intention of the inventor to embody within the patent warranted heron all changes and modifications as reasonably and properly come within the scope of his contribution to the art.

The invention claimed is:

1. An implantable medical device comprising:
an event detector that detects occurrence of a predefined heart event in a detection time window from start of a heart cycle of a heart up to opening of aortic valves in said heart cycle, said detected predefined event is assigned a time reference;
an onset detector that detects an onset of ventricular filling of said heart in said heart cycle;
a timing processor that determines a relative time of said detected onset of ventricular filling based on said assigned time reference;
a heart failure processor that generates detection data indicative of an increased risk of heart failure of a subject based on said determined relative time;
a signal applier that applies a current or voltage signal over at least a portion of said heart via two electrodes;
a signal measurer that measures a resulting voltage or current signal over between said two electrodes;
an impedance processor that determines an impedance signal based on said applied current or voltage signal and said measured resulting voltage or current signal, wherein said onset detector detecting said onset of ventricular filling based on said impedance signal.
a time assigner that assigns a zero time reference to said detected predefined event:
said timing processor comprising a sample counter that counts a number of samples in said impedance signal from said occurrence of said predefined event up to said onset of ventricular filling; and
said timing processor comprising a time converter that determines said relative time of said detected onset of ventricular filling by dividing said counted number of samples with a sampling frequency of said impedance processor.

2. The device according to claim 1, further comprising a time assigner that assigns said time reference to said detected predefined event.

3. The device according to claim 1, wherein said event detector comprises a QRS detector that detects occurrence of a QRS complex during said detection time window based on an electric signal sensed from a heart of said subject.

4. The device according to claim 1, wherein said signal applier applies said current or voltage signal during at least one respiratory cycle of said subject and wherein said impedance processor determines a respective impedance signal for each complete heart cycle occurring during said at least one respiratory cycle and determines an average impedance signal based on said respective impedance signals.

5. The device according to claim 1, wherein said signal applier applies said current or voltage signal during multiple respiratory cycles of said subject, said implantable medical device further comprising a heart cycle detector that detects, based on said impedance signal, multiple heart cycles occurring at a predefined respiratory phase, and wherein said impedance processor determines a respective impedance signal for each heart cycle of said multiple heart cycles and determines an average impedance signal based on said respective impedance signals.

6. The device according to claim 1, comprising:
a signal applier that applies a current or voltage signal over at least a portion of said heart via two electrodes;
a signal measurer that measures a resulting voltage or current signal between said two electrodes;
an impedance processor that determines an impedance signal based on said applied current or voltage signal and said measured resulting voltage or current signal, said onset detector detecting said onset of ventricular filling based on said impedance signal; and said volume detector comprising a maximum detector that detects a maximum of said impedance signal during said heart cycle, wherein said maximum is indicative of said minimum blood volume.

7. An implantable medical device comprising:

an event detector that detects occurrence of a predefined heart event in a detection time window from start of a heart cycle of a heart up to opening of aortic valves in said heart cycle, said detected predefined event is assigned a time reference;

an onset detector that detects an onset of ventricular filling of said heart in said heart cycle;

a timing processor that determines a relative time of said detected onset of ventricular filling based on said assigned time reference; and a heart failure processor that generates detection data indicative of an increased risk of heart failure of a subject based on said determined relative time; and further comprising:

a volume detector that detects occurrence of a minimum blood volume in a ventricle of said heart during said heart cycle, wherein said timing processor determines a relative time of said detected minimum blood volume based on said assigned time reference; and a cardiac reserve processor that generates detection data indicative of a cardiac reserve of said heart based on said relative time of said detected minimum blood volume and said relative time of said onset of ventricular filling.

8. An implantable medical device comprising:

an event detector that detects occurrence of a predefined heart event in a detection time window from start of a heart cycle of a heart up to opening of aortic valves in said heart cycle, said detected predefined event is assigned a time reference;

an onset detector that detects an onset of ventricular filling of said heart in said heart cycle;

a timing processor that determines a relative time of said detected onset of ventricular filling based on said assigned time reference; and a heart failure processor that generates detection data indicative of an increased risk of heart failure of a subject based on said determined relative time; and further comprising a time comparator that compares said determined relative time with a time threshold, and wherein said heart failure processor generates said detection data based on said comparison.

9. The device according to claim 8, further comprising a threshold determiner that determines said time threshold based on a previously determined relative time of said detected onset of ventricular filling.

10. The device according to claim 8, further comprising a threshold updater that updates said time threshold based on said determined relative time if said time threshold does not exceed said determined relative time with said at least a minimum time value.

* * * * *